(12) United States Patent
Akihiro

(10) Patent No.: US 10,888,449 B2
(45) Date of Patent: Jan. 12, 2021

(54) NASAL DEVICE

(71) Applicant: Shu-Chen Tsai, Taipei (TW)

(72) Inventor: Yoshiaki Akihiro, Taipei (TW)

(73) Assignee: Shu-Chen Tsai, Taipei (TW)

( * ) Notice: Subject to any disclaimer, the term of this patent is extended or adjusted under 35 U.S.C. 154(b) by 112 days.

(21) Appl. No.: 16/264,858

(22) Filed: Feb. 1, 2019

(65) Prior Publication Data

US 2020/0206012 A1 Jul. 2, 2020

(30) Foreign Application Priority Data

Dec. 28, 2018 (TW) .................................. 107147767

(51) Int. Cl.
*A61F 5/08* (2006.01)

(52) U.S. Cl.
CPC ...................................... *A61F 5/08* (2013.01)

(58) Field of Classification Search
CPC ... A62B 23/06; A61F 5/08; A61F 5/56; A61F 2/18; A61F 2/186; A61F 13/126; A61F 2/00; A61F 2/02; A61F 5/00; A61F 5/01; A61M 15/08; A61M 15/085; A61M 16/0666; A61M 15/00; A61M 16/00; A61M 16/20; A61M 16/201; A61M 16/0093; A61B 17/12104; A61B 2017/246
See application file for complete search history.

(56) References Cited

U.S. PATENT DOCUMENTS

| | | | |
|---|---|---|---|
| 8,262,688 B2 | 9/2012 | Santin et al. | |
| 2003/0195552 A1* | 10/2003 | Santin | A61F 5/08 606/199 |
| 2004/0059368 A1* | 3/2004 | Maryanka | A61M 29/00 606/191 |
| 2009/0007919 A1* | 1/2009 | Dolezal | A62B 7/10 128/206.11 |
| 2009/0194100 A1* | 8/2009 | Minagi | 128/200.24 |
| 2013/0081637 A1* | 4/2013 | Foley et al. | A61F 5/56 |

FOREIGN PATENT DOCUMENTS

| | | |
|---|---|---|
| CN | 1953778 B | 7/2011 |
| CN | 104619377 A | 5/2015 |
| CN | 204699271 U | 10/2015 |

OTHER PUBLICATIONS

Search Report from corresponding Taiwanese Patent Application No. 107147767, dated Jun. 6, 2019.

* cited by examiner

*Primary Examiner* — Ashley L Fishback
*Assistant Examiner* — Uyen N Vo
(74) *Attorney, Agent, or Firm* — Harness, Dickey & Pierce, P.L.C.

(57) ABSTRACT

This invention provides a nasal device comprising: a main body being tubular in shape having a hollow structure which extends from the end of front side to the end of rear side, wherein the main body is insertable into a nasal cavity; a front opening portion at the end of a front side of the main body and is configured to open the hollow structure towards the outside of the nasal device; a rear opening portion at the end of a rear side of the main body and is configured to open the hollow structure towards the outside of the nasal device; and a pressing portion placed at the rear end of the main structure and can move sideways from the rear end view in between a protruding position of the main body and an overlapping position that overlaps with the hollow structure.

7 Claims, 3 Drawing Sheets

NASAL DEVICE

CROSS-REFERENCE TO RELATED APPLICATIONS

This application claims priority to Taiwanese application No. 107147767 filed Dec. 28, 2018, the entire contents of which are hereby incorporated by reference.

FIELD

This invention provides a nasal device to be placed inside the nasal cavity while breathing.

BACKGROUND

Sleep apnea syndrome, characterized by frequent pauses in breathing during sleep, is a common occurrence in the general population. When symptoms of sleep apnea occur, reduction-oxidation reactions in blood are insufficient, causing oxygen deficiency when blood circulates to brain. Therefore, it causes bad influences on not only the cranial nerve tissue, but also on the hormone metabolism. Moreover, it may increase risks of lifestyle diseases such as heart attack, diabetes or cerebral vascular disease.

The traditional method of inserting a nasal expander into nasal cavity during sleep to relieve the symptoms of sleep apnea syndrome is disclosed in prior art. This type of nasal expander is placed inside nasal cavity while expanded to improve airflow into nostrils.

However, the traditional nasal device needs to further enlarge the nasal cavity to pass more air through the airway. A bigger nasal device is required in order to enlarge the nasal cavity, in which such large-sized nasal device is more difficult to be placed inside the nasal cavity. On the other hand, if the nasal device is made smaller, although it is easier to be placed inside the nasal cavity, the device cannot enlarge nor enable more air to enter inside the nasal cavity. The nasal device might also fall out of the nasal cavity easily. Therefore, it is difficult for the traditional nasal device to achieve (i) easy insertion, (ii) more air to be led into the airway, and (iii) prevention from falling out at the same time.

SUMMARY

This invention aims to provide a nasal device, which is easy to be placed inside the nasal cavity, allows sufficient air to pass through the nasal cavity and enter the respiratory tract when being inserted into the nasal cavity, and prevents the device from slipping out of the nasal cavity.

A nasal device for use while breathing and adapted for insertion within a human nasal cavity, the device comprising: a main body being tubular in shape having a hollow structure which extends from the end of front side to the end of rear side, wherein the main body is insertable into a nasal cavity; a front opening portion at the end of a front side of the main body and is configured to open the hollow structure towards the outside of the nasal device; a rear opening portion at the end of a rear side of the main body and is configured to open the hollow structure towards the outside of the nasal device; and a pressing portion placed at the rear end of the main structure and can move sideways from the rear end view in between a protruding position of the main body and an overlapping portion that overlaps with the hollow structure.

A user may insert the main body into the nasal cavity while the pressing portion is in overlapping position. When the device is inserted in the nasal cavity, the pressing portion may be moved from the overlapping position to the protruding position; the pressing portion then presses the inner wall of the nasal cavity. Further to the aforesaid action of the pressing portion presses the inner wall of nasal cavity, the inner wall of the opposite side of the nasal cavity is pressed by the main body; thus enlarging the entire nasal cavity. Therefore, the air induced from the rear end opening to the hollow structure is discharged from the front end opening to the respiratory tract.

BRIEF DESCRIPTION OF DRAWINGS

Some of the embodiments will be described in detail, with references to the following figures, wherein like designations denote like members, wherein.

DETAILED DESCRIPTION

Figure 1:
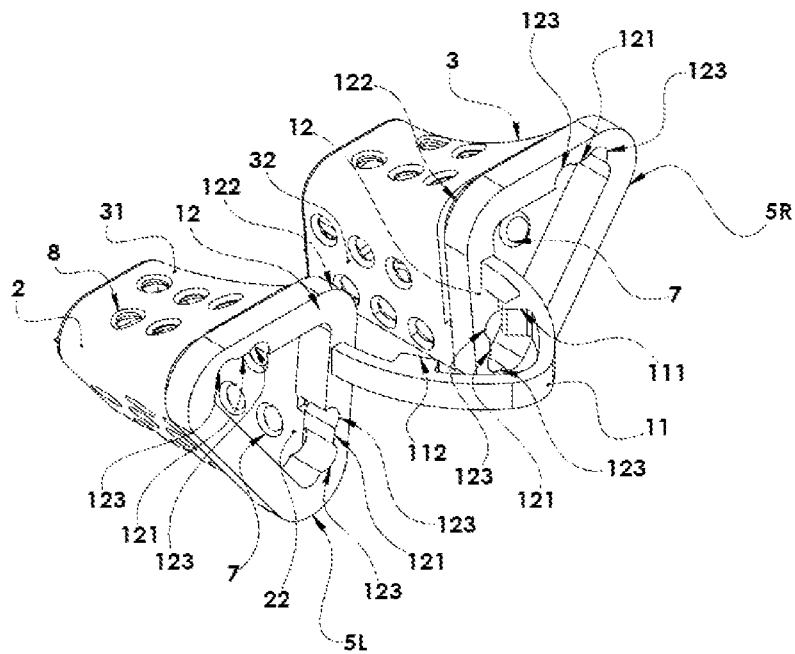
FIG. 1 is an oblique view from above of the nasal device in accordance with the embodiment of the present invention.
Figure 2:
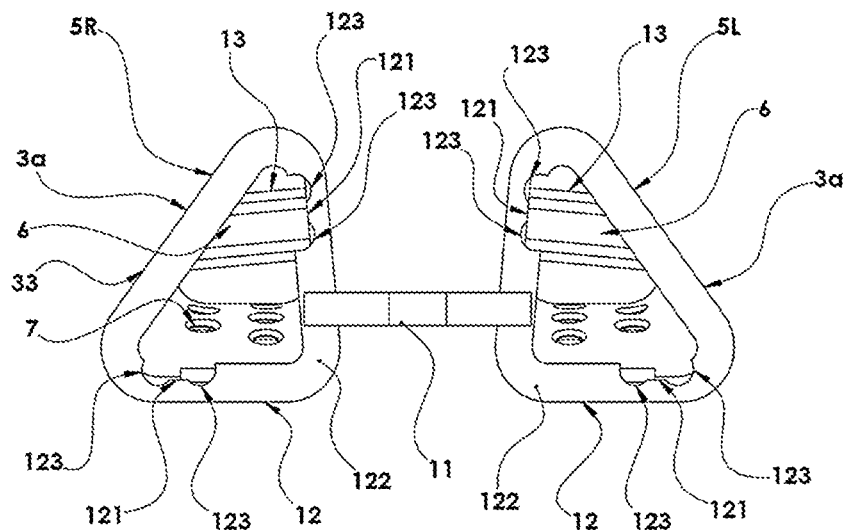
FIG. 2 is a front view of the pressing portion moving to the protruding position of the nasal device in accordance with the embodiment of the present invention.
Figure 3:
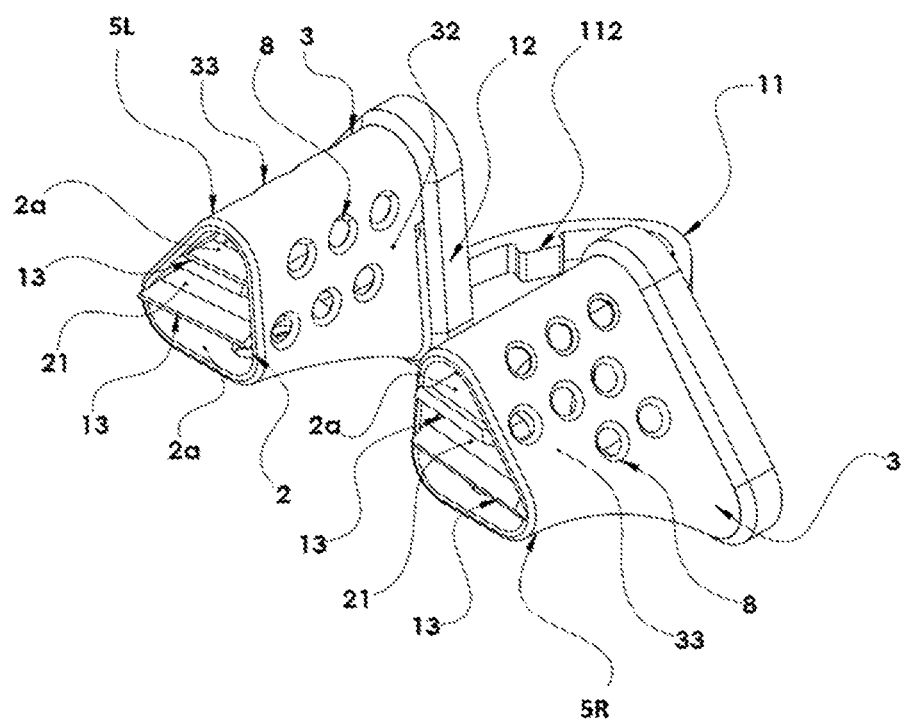
FIG. 3 is an oblique view from below of the nasal device in accordance with the embodiment of the present invention.

The embodiments below are used for illustrating the objectives and effects of embodiments of the present invention, and are not to be construed as constituting any limitations of the invention. Figures are illustrated with description using orthogonal coordinate system of X axis, Y axis and Z axis. The positive direction of Y axis is forward, while the negative direction of Y axis is backward; the positive direction of X axis is right, while the negative direction of X axis is left; and the positive direction of Z axis is upward and negative direction of Z axis is downward.

[The Composition of the Nasal Device]

Referring to FIGS. 1 to 6, the nasal device 1 in the embodiment of the present invention is described below.

The nasal device 1 is integrally formed from elastic synthetic resin and the entire device exhibits elastic deformation. Examples of synthetic resin in the nasal device 1 that may be used include, but are not limited to: styrene elastomer, polyester elastomer, silicon, polyethylene and polyvinyl chloride.

The nasal device 1 comprises a left main body 5L that is insertable into the left nasal cavity, a right main body 5R that is insertable into the right nasal cavity, and a connecting member 11 that connects the left main body 5L and the right main body 5R. Both the left main body 5L and the right main body 5R are symmetric in appearance. The left main body 5L and the right main body 5R are both tubular in shape, and the end 3a of the rear side 3 of each main body becomes narrower towards the end 2a of the front side 2 having a smaller diameter, which results in a cone-shaped main body. The main body is insertable into the nasal cavity from the front side 2. More specifically, the left main body 5L and the right main body 5R each comprises a hollow structure 6, internal concave parts 7, external concave parts 8, pathways 9, guiding plates 13, a pressing portion 12, a front opening portion 21 and a rear opening portion 22.

The hollow structure 6 located inside the left main body 5L and the right main body 5R extends from the end 2a of the front side 2 to the end 3a of the rear side 3, and the end 3a of the rear side 3 becomes narrower towards the end 2a of the front side 2 having a smaller diameter. The hollow structure 6 is surrounded by the first wall 31 in bilateral direction (left-right direction), the second wall 32 in vertical direction and the third wall 33. The first wall 31 and the second wall 32 are connected by their ends in the mutually vertical extending direction. The third wall 33 connects the first wall 31 and the second wall 32. The third wall 33 of the left main body 5L curves towards the right into a convex shape. The third wall 33 of the right main body 5R curves towards the left into a convex shape. The connecting member of the first wall 31 and the second wall 32, the connecting member of the first wall 31 and the third wall 33, and the connecting member of the second wall 32 and the third wall 33 are all in a curved shape respectively.

The front opening portion 21 in the end 2a of the front side 2 opens the hollow structure 6 towards the outside of the device. The rear opening portion 22 in the end 3a of the rear side 3 opens the hollow structure 6 towards the outside of the device. The inner diameter of the rear opening portion 22 is larger than that of the front opening portion 21.

The pressing portion 12 is located at the end side 3 of the left main body 5L and the end side 3 of the right main body 5R respectively. The pressing portion 12 of the left main body 5L can move sideways in the right direction between the protruding position of the left main body 5L (shown in FIG. 2) and the overlapping position of the hollow structure 6 (shown in FIG. 6) from the rear end 3 view. Further, the left main body 5L presses the musculus depressor septi nasi at the protruding position when the device is inserted into the nasal cavity. Moreover, the pressing portion 12 of the right main body 5R can move sideways in the left direction between the protruding position of the right main body 5R (shown in FIG. 2) and the overlapping position of the hollow structure 6 (shown in FIG. 6) from the rear end 3 view. Further, the right main body 5R presses the musculus depressor septi nasi at the protruding position when the device is inserted into the nasal cavity.

The pressing portion 12 comprises a middle portion 121, a protruding portion 122 and a hinge member portion 123. The middle portion 121 is placed in between a pair of hinge member portions 123. The protruding portion 122 is thicker than the thickness of the middle portion 121 and wider than the width of the middle portion 121 in the anteroposterior direction (front-rear direction). It presses the musculus depressor septi nasi when the pressing portion 12 moves toward the protruding position. The hinge member portion 123 is thinner than the middle portion 121 and the protruding portion 122, whereas the width in the anteroposterior direction (front-rear direction) is the same as the width of the middle portion 121 in the anteroposterior direction (front-rear direction). The hinge member 123 is placed in between the middle portion 121 and the protruding portion 122, and also in between the middle portion 121 and the left main body 5L or the right main body 5R.

From the protruding position viewed from the rear end 3, the pressing portion 12 is not restricted to the condition that the protruding portion 122 partially protrudes sideways from the left main body 5L and the right main body 5R. The protruding portion 122 may also totally protrude sideways from the left main body 5L and the right main body 5R.

Moreover, from the overlapping position viewed from the rear end 3, the pressing portion 12 is not restricted to the condition that the protruding portion 122 totally overlaps with the hollow structure 6. The protruding portion 122 may also partially overlap with the hollow structure 6.

Figure 5:
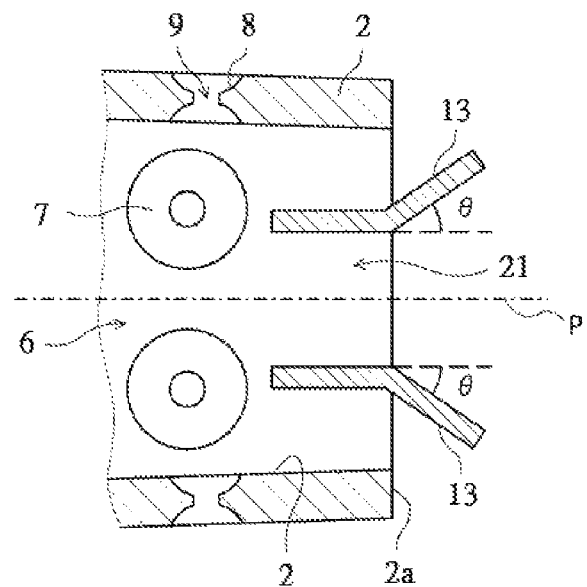
FIG. 5 is an enlarged cross-sectional view of front end of the main body of the nasal device in accordance with the embodiment of the present invention.

Guiding plates 13 are in tabular shape and work in pairs. Guiding plates 13 are located at the inner surface of the hollow structure 6 at the front side 2, and they extend outwardly towards the outside of the device in a direction away from each other. A pair of guiding plates 13 in FIG. 5 is inclined at a certain angle of inclination against the axis a of the hollow structure 6. In this embodiment, the certain degree of inclination angle may preferably be from 0° to 30°.

Figure 4:
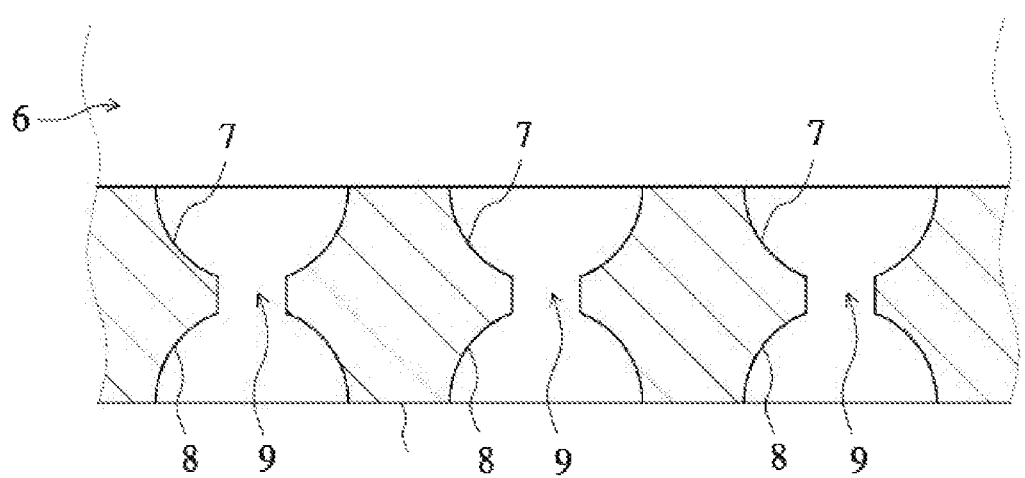
FIG. 4 is an enlarged cross-sectional view of the main body of the nasal device in accordance with the embodiment of the present invention.

The internal concave part 7 in FIG. 4 is a bowl-shaped concave part formed by gouging the inner surface surrounding the hollow structure 6, wherein a plurality of internal concave parts are located at the inner surface.

The external concave part 8 in FIG. 4 is a bowl-shaped concave part formed by gouging the external surface of the left main body 5L and the right main body 5R, wherein a plurality of concave parts are located at the opposite side of the internal concave part 7.

The pathway 9 in FIG. 4 connects the hollow structure 6 to the outside of the device, wherein one end is the opening of the internal concave part 7 and the other end is the opening of the external concave part 8.

The connecting member 11 connects the pressing portion 12 of the left main body 5L and the pressing portion 12 of the right main body 5R. The connecting member 11 comprises a control unit 111 and a contacting unit 112; the control unit 111 has an apical front end surface that protrudes in a direction facing the contacting unit 112; the contacting unit 112 has a flat front end surface that protrudes in a direction facing the control unit 111.

The configuration of the nasal device 1 can be altered according to the user by changing the overall size of the left main body 5L and the right main body 5R. More specifically, the overall size of the left main body 5L and the right main body 5R of the nasal device 1 for children and females will be smaller than the nasal device 1 for males.

[Operation of Nasal Device]

Referring to FIGS. 1 to 6, the operation of the nasal device 1 in this invention is described in details below.

Figure 6:
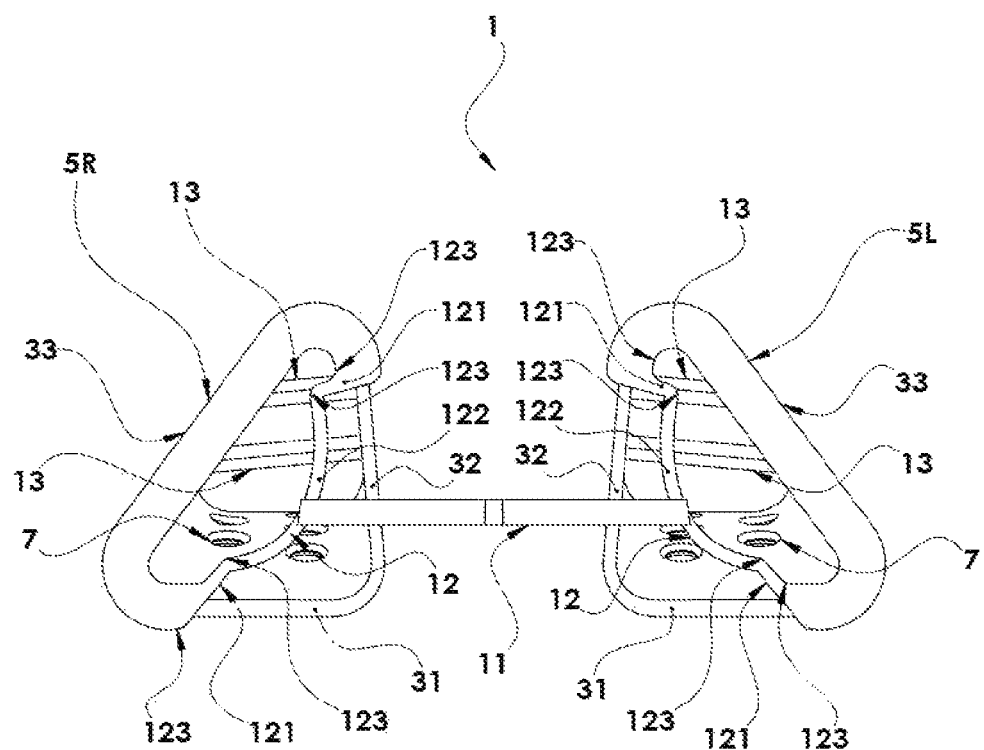
FIG. 6 is a front view of the pressing portion moving to the overlapping portion of the nasal device in accordance with the embodiment of the present invention.

As shown in the nasal device 1 of FIG. 1, bending the hinge member 123 causes the pressing portion 12 to be in an overlapping position shown in FIG. 6. The left main body 5L is inserted into the left side of the nasal cavity from the front end 2, whereas the right main body 5R is inserted into the right side of the nasal cavity from the front end 2. Meanwhile, it may be easier to insert the nasal device into the nasal cavity by placing the pressing portion at the overlapping position.

After the left main body 5L and the right main body 5R are placed inside the nasal cavity, by pulling the connecting member 11 in a forward direction and stretching the bended hinge member 123, the pressing portion 12 moves from the overlapping position to the protruding position. Meanwhile, the movement of the pressing portion 12 moving from the overlapping position to the protruding position can be done by an action of the hinge member 123 positioned at the pressing portion 12. Moreover, the connecting member 11 controls the movement of the control unit 111 and the contacting unit 112 facing each other by contacting the control unit 111 and the contacting unit 112, and prevents unnecessarily operations. Therefore, the pressing portion 12 can easily be moved from the overlapping position to the protruding position by the connecting member 11.

The pressing portion 12 moves from the overlapping position to the protruding position and causes the pressing portion 12 whereby the left main body 5L and the right main body 5R press against the inner wall of the nasal cavity. The pressing portion also presses the musculus depressor septi nasi. Therefore, the nasal device 1 can enlarge the nasal cavity and prevent the nasal device 1 from slipping out of the nasal cavity. Moreover, the pressing portion 12 presses the musculus depressor septi nasi and enlarges the capacity of the nasal cavity from below. It can lead more external air through the nasal cavity, exhale more air to the outside through the nasal cavity, elevate the tongue to the palate; thus stopping breathing through the mouth and preventing snoring. Furthermore, the counter force of the pressing portion 12 pressing on the inner wall of the nasal cavity enables the pressing portion 12 to press on the inner wall of the opposite side of the inner wall of the nasal cavity. Pressing the left main body 5L and the right main body 5R can enlarge the nasal cavity and prevent the nasal device 1 from slipping out of the nasal cavity.

The left main body 5L and the right main body 5R are formed by the vertically connected first wall 31 and second wall 32 and a third wall 33 protruding on a side into curved shape. The device body is consistent with the shape of the nasal cavity; hence it can enlarge the capacity of the nasal cavity and prevent it from slipping out of the nasal cavity.

The end 3a of the rear side 3 gets narrower towards the end 2a of the front side 2 and forms the hollow structure 6. When breathing with the nasal device 1 inserted in the nasal cavity, outside air flows from the rear opening portion 22 into the hollow structure 6, and the airflow speeds up from the end 3a of the rear side 3 of the hollow structure 6 to the end 2a of the front side 2, then exits through the front opening portion 21 to the outside of the nasal cavity. It leads sufficient air through the nasal cavity and into the respiratory tract.

Moreover, air flows through the hollow structure 6 and a turbulent flow is created by the spiral-shaped internal concave part 7, which accelerates the flow rate of air in the hollow structure 6.

Additionally, the movement of air in the internal concave part 7 causes the air in the external concave part 8 and the pathway 9 to be sucked into the internal concave part 7. Comparing to the internal concave part 7, the external concave part 8 and the pathway 9 form a negative pressure, thus allowing the mucus secreted from nose to evaporate to the external concave part 8 and the pathway 9 easily. The mucus evaporated to the external concave part 8 and the pathway 9 is drawn into the internal concave part 7 and reaches the hollow structure 6, and furthermore enters into the deep parts of the nasal cavity or mucosa tissue of the pharynx by airflow in the hollow structure 6. Therefore, the deep parts of the nasal cavity or mucosa tissue of the pharynx may remain moist and protect their functions.

Moreover, the flow rate of air exhaled from the nasal cavity through the front opening portion 21 can be accelerated by guiding plates 13, and guiding plates 13 can guide the air discharged from the front opening portion 21 to the middle meatus of nose and help in exhalation out. The air can be lead into the larynx without reducing the speed. It has been hereby experimentally confirmed that by having a pair of guiding plates 13 inclining 30 degrees with the axis P of the hollow structure 6, the flow rate of air exhaled from the nasal cavity through the front opening portion 20 can be accelerated.

The nasal device 1 can accelerate the airflow rate when air flows into the nasal cavity, thereby accelerate the airflow rate entering the lungs and further inflate the pulmonary alveoli. Moreover, by further inflating the pulmonary alveoli, the elastic recoil of the alveoli is more effective in deflating the pulmonary alveoli and accelerating the flow rate of exhaled air. It can also reduce the turbidity caused by the pause between inhalation and exhalation while air passes through bronchi, thereby increase the respiratory capacity and peripheral capillary oxygen saturation (SpO2).

Additionally, the pressing portion 12 presses the inner wall of nasal cavity in an outward direction and allows the surrounding musculature of the nasal cavity to expand.

When the nasal device 1 is removed from the nasal cavity, the connecting member 11 is operated in a parting direction of the control unit 111 and the contacting unit 112 (separating the control unit 111 and the contacting unit 112), wherein the pressing portion 12 moves from the protruding position to the overlapping position, hence lessens the force of the pressing portion 12 on the inner wall of the nasal cavity. Therefore, the movement of the pressing portion 12 moving from the protruding position to the overlapping position can be achieved by an action of the hinge member 123 positioned at the pressing portion 12, and easily remove the nasal device 1 from the nasal cavity. Moreover, the connecting member 11 can easily move the pressing portion 12 from the protruding position to the overlapping position.

Therefore, according to this embodiment, the device comprises a hollow structure 6 that extends from the end 2a of the front side 2 to the end 3a of the rear side 3, the rear side 3 of the left main body 5L and the right main body 5R that is inserted into the nasal cavity simultaneously, and the pressing portion 12 that can move sideways from the rear end view in between a protruding position of the left main body 5L or the right main body 5R and an overlapping position that overlaps with the hollow structure 6. Such configuration can assist the nasal device to be easily placed inside the nasal cavity and allows sufficient air to pass through the airway and prevents the device from slipping out of the nasal cavity.

According to this embodiment, the connecting member 11 connects the left main body 5L and the right main body 5R and prevents any of the left main body 5L or right main body 5R from being lost or forgotten to bring by a user.

Although the invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

More specifically, in the aforementioned embodiment, the left main body 5L and the right main body 5R can be used separately without using the connecting member 11.

Moreover, although the pressing portion 12 presses the musculus depressor septi nasi, the pressing portion 12 can also press the inner wall of the nasal cavity other than the musculus depressor septi nasi.

Moreover, the location where the pressing portion 12 connects with the connecting member 11 acts as a boundary, wherein two hinge members 123 of the pressing portion 12 are respectively positioned on each side. However, the location where the pressing portion 12 connects with the connecting member 11 acts as a boundary, wherein one or more than three hinge members 123 of the pressing portion 12 may also be respectively positioned on each side.

What is claimed is:

1. A nasal device for use while breathing and adapted for insertion within a human nasal cavity, the device comprising:
   a main body being tubular in shape having a hollow structure which extends from the end of front side to the end of rear side, wherein the main body is insertable into a nasal cavity; and
   a front opening portion at the end of a front side of the main body and is configured to open the hollow structure towards the outside of the nasal device; and
   a rear opening portion at the end of a rear side of the main body and is configured to open the hollow structure towards the outside of the nasal device; and
   a pressing portion placed at the rear end of the main body and can move sideways from the rear end view in between a protruding position of the main body and an overlapping position that overlaps with the hollow structure,
   wherein the main body comprises a plurality of internal concave parts on an inner surface surrounding the hollow structure, a plurality of external concave parts and a plurality of connecting holes, further wherein the external concave part is formed by concaving on an outer surface surrounding the hollow structure, and the connecting hole connects to the outside by having one end at the internal concave part and the other end at the external concave part.

2. The nasal device of claim 1, wherein the main body comprises the hollow structure surrounded by a first wall, a second wall and a third wall, further wherein the first wall and the second wall are connected vertically; the third wall connects the first wall and the second wall and configured to form into a protruding curved shape on a side face; and the pressing portion protrudes on a side towards the first wall and the second wall from the protruding position of the rear end view.

3. The nasal device of claim 1, wherein the pressing portion presses a musculus depressor septi nasi at the protruding position when the main body is inserted inside the nasal cavity.

4. The nasal device of claim 1, wherein a connecting member is connected to a pair of pressing portions positioned separately in the main body, enabling the pressing portion to move between the protruding position and the overlapping position.

5. The nasal device of claim 1, wherein the pressing portion comprises a hinge member; and the hinge member bends while moving from the protruding position to the overlapping position, and stretches while moving from the overlapping position to the protruding position.

6. The nasal device of claim 1, wherein the hollow structure is in a shape that the perimeter of the rear end becomes narrower from the rear end towards the front end, with the perimeter of the front end having a smaller opening.

7. The nasal device of claim 1, wherein the main body comprises a plurality of guiding plates, characterized in that the plurality of guiding plates are placed at the front end and extends outwardly in the opposite direction from the front opening portion to the outside of the nasal device.

* * * * *